United States Patent
Albertorio et al.

(10) Patent No.: US 9,204,960 B2
(45) Date of Patent: Dec. 8, 2015

(54) ADJUSTABLE SUTURE-BUTTON CONSTRUCTS FOR LIGAMENT RECONSTRUCTION

(71) Applicant: Arthrex, Inc., Naples, FL (US)

(72) Inventors: Ricardo Albertorio, Naples, FL (US); Jacob A. Jolly, Bonita Springs, FL (US); Eric S. Zajac, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 14/087,703

(22) Filed: Nov. 22, 2013

(65) Prior Publication Data

US 2014/0074239 A1   Mar. 13, 2014

Related U.S. Application Data

(62) Division of application No. 13/298,939, filed on Nov. 17, 2011, now Pat. No. 8,591,578.

(60) Provisional application No. 61/414,715, filed on Nov. 17, 2010.

(51) Int. Cl.
*A61F 2/08* (2006.01)
*A61B 17/04* (2006.01)

(52) U.S. Cl.
CPC ........... *A61F 2/0811* (2013.01); *A61B 17/0401* (2013.01); *A61F 2/08* (2013.01); *A61B 2017/0404* (2013.01); *A61B 2017/0459* (2013.01); *A61B 2017/0477* (2013.01);
(Continued)

(58) Field of Classification Search
CPC . A61F 2/08; A61F 2/0811; A61F 2002/0882; A61F 2002/0852
See application file for complete search history.

(56) References Cited

U.S. PATENT DOCUMENTS 3,176,316 A   4/1965 Bodell
3,409,014 A   11/1968 Shannon
(Continued)

FOREIGN PATENT DOCUMENTS

DE   299 10 202 U1   9/1999
DE   199 26 626   12/2000
(Continued)

OTHER PUBLICATIONS

Eric McCarty, M.D., "ZipTight Fixation System Featuring ZipLoop Technology, Acute AC Joint Reconstruction," Biomet Sports Medicine, 2010.

Primary Examiner — Bruce E Snow
(74) Attorney, Agent, or Firm — Dickstein Shapiro LLP

(57) ABSTRACT

An adjustable suture-button construct for ligament reconstruction. The construct is a knotless, adjustable, flexible suture loop, a first fixation device (a free or removable slotted button) and optionally a second fixation device (a fixed, non-removable button). Suture ends of the knotless suture loop provide a variable-length graft support that can be adjusted prior to, during, or after deployment of the constructs. The removable, detachable fixation device is provided with attachment feature(s) to permit assembly onto the adjustable loop. The removable, detachable fixation device is attached to the tibia end of the loop construct after the loop construct is passed through the tibial tunnel (i.e., once the loop exits the anterior tibia cortex). If a fixed, non-removable button is employed, the fixed, non-removable button is securely attached (by stitching, for example) to the graft.

2 Claims, 14 Drawing Sheets

(52) U.S. Cl.
CPC ....... *A61F2/0805* (2013.01); *A61F 2002/0852* (2013.01); *A61F 2002/0882* (2013.01)

(56) References Cited

U.S. PATENT DOCUMENTS

| | | |
|---|---|---|
| 4,187,558 A | 2/1980 | Dahlen et al. |
| 4,301,551 A | 11/1981 | Dore et al. |
| 4,400,833 A | 8/1983 | Kurland |
| 4,776,851 A | 10/1988 | Bruchman et al. |
| 4,790,850 A | 12/1988 | Dunn et al. |
| 4,792,336 A | 12/1988 | Hlavacek et al. |
| 4,851,005 A | 7/1989 | Hunt et al. |
| 4,863,471 A | 9/1989 | Mansat |
| 4,917,700 A | 4/1990 | Aikins |
| 4,932,972 A | 6/1990 | Dunn et al. |
| 5,024,669 A | 6/1991 | Peterson et al. |
| 5,026,398 A | 6/1991 | May et al. |
| 5,129,902 A | 7/1992 | Goble et al. |
| 5,171,274 A | 12/1992 | Fluckiger et al. |
| 5,211,647 A | 5/1993 | Schmieding |
| 5,217,495 A | 6/1993 | Kaplan et al. |
| 5,263,984 A | 11/1993 | Li et al. |
| 5,266,075 A | 11/1993 | Clark et al. |
| 5,306,301 A | 4/1994 | Graf et al. |
| 5,320,626 A | 6/1994 | Schmieding |
| 5,397,357 A | 3/1995 | Schmieding et al. |
| 5,417,699 A | 5/1995 | Klein et al. |
| 5,562,669 A | 10/1996 | McGuire |
| 5,575,819 A | 11/1996 | Amis |
| 5,628,756 A | 5/1997 | Barker et al. |
| 5,643,266 A | 7/1997 | Li |
| 5,645,588 A | 7/1997 | Graf et al. |
| 5,931,869 A | 8/1999 | Boucher et al. |
| 5,961,520 A | 10/1999 | Beck et al. |
| 5,964,764 A | 10/1999 | West, Jr. et al. |
| 6,056,752 A | 5/2000 | Roger |
| 6,099,530 A | 8/2000 | Simonian et al. |
| 6,099,568 A | 8/2000 | Simonian et al. |
| 6,110,207 A | 8/2000 | Eichhorn et al. |
| 6,159,234 A | 12/2000 | Bonutti et al. |
| 6,193,754 B1 | 2/2001 | Seedhom |
| 6,203,572 B1 | 3/2001 | Johnson et al. |
| 6,283,996 B1 | 9/2001 | Chervitz et al. |
| 6,296,659 B1 | 10/2001 | Foerster |
| 6,325,804 B1 | 12/2001 | Wenstrom et al. |
| 6,517,578 B2 | 2/2003 | Hein |
| 6,533,802 B2 | 3/2003 | Bojarski et al. |
| 7,097,654 B1 | 8/2006 | Freedland |
| 7,494,506 B2 | 2/2009 | Brulez et al. |
| 7,686,838 B2 | 3/2010 | Wolf et al. |
| 7,749,250 B2 | 7/2010 | Stone et al. |
| 7,776,039 B2 | 8/2010 | Bernstein et al. |
| 7,819,898 B2 | 10/2010 | Stone et al. |
| 7,828,855 B2 | 11/2010 | Ellis et al. |
| 7,875,057 B2 | 1/2011 | Cook et al. |
| 7,905,903 B2 | 3/2011 | Stone et al. |
| 7,914,539 B2 | 3/2011 | Stone et al. |
| 8,109,965 B2 | 2/2012 | Stone et al. |
| 8,118,836 B2 | 2/2012 | Denham et al. |
| 8,162,997 B2 | 4/2012 | Struhl |
| 8,206,446 B1 | 6/2012 | Montgomery |
| 8,231,654 B2 | 7/2012 | Kaiser et al. |
| 2001/0041938 A1 | 11/2001 | Hein |
| 2002/0161439 A1 | 10/2002 | Strobel et al. |
| 2003/0114929 A1 | 6/2003 | Knudsen et al. |
| 2004/0015171 A1 | 1/2004 | Bojarski et al. |
| 2004/0059415 A1 | 3/2004 | Schmieding |
| 2004/0073306 A1 | 4/2004 | Eichhorn et al. |
| 2004/0243235 A1 | 12/2004 | Goh et al. |
| 2004/0267360 A1 | 12/2004 | Huber |
| 2005/0004670 A1 | 1/2005 | Gebhardt et al. |
| 2005/0033363 A1 | 2/2005 | Bojarski et al. |
| 2005/0065533 A1 | 3/2005 | Magen et al. |
| 2005/0070906 A1 | 3/2005 | Clark et al. |
| 2005/0137704 A1 | 6/2005 | Steenlage |
| 2005/0149187 A1 | 7/2005 | Clark et al. |
| 2005/0171603 A1 | 8/2005 | Justin et al. |
| 2005/0203623 A1 | 9/2005 | Steiner et al. |
| 2005/0261766 A1 | 11/2005 | Chervitz et al. |
| 2006/0067971 A1 | 3/2006 | Story et al. |
| 2006/0095130 A1 | 5/2006 | Caborn et al. |
| 2006/0142769 A1 | 6/2006 | Collette |
| 2006/0265064 A1 | 11/2006 | Re et al. |
| 2007/0021839 A1 | 1/2007 | Lowe |
| 2007/0083236 A1 | 4/2007 | Sikora et al. |
| 2007/0118217 A1 | 5/2007 | Brulez et al. |
| 2007/0162123 A1 | 7/2007 | Whittaker et al. |
| 2007/0162125 A1 | 7/2007 | LeBeau et al. |
| 2007/0179531 A1 | 8/2007 | Thornes |
| 2007/0225805 A1 | 9/2007 | Schmieding |
| 2007/0239209 A1 | 10/2007 | Fallman |
| 2007/0239275 A1 | 10/2007 | Willobee |
| 2007/0250163 A1 | 10/2007 | Cassani |
| 2007/0270857 A1 | 11/2007 | Lombardo et al. |
| 2008/0046009 A1 | 2/2008 | Albertorio et al. |
| 2008/0177302 A1 | 7/2008 | Shurnas |
| 2008/0188935 A1 | 8/2008 | Saylor et al. |
| 2008/0188936 A1 | 8/2008 | Ball et al. |
| 2008/0208252 A1 | 8/2008 | Holmes |
| 2008/0215150 A1 | 9/2008 | Koob et al. |
| 2008/0228271 A1 | 9/2008 | Stone et al. |
| 2008/0234819 A1 | 9/2008 | Schmieding et al. |
| 2008/0243248 A1 | 10/2008 | Stone et al. |
| 2008/0275553 A1 | 11/2008 | Wolf et al. |
| 2008/0275554 A1 | 11/2008 | Iannarone et al. |
| 2008/0287991 A1* | 11/2008 | Fromm .................. 606/232 |
| 2008/0300683 A1 | 12/2008 | Altman et al. |
| 2008/0312689 A1 | 12/2008 | Denham et al. |
| 2009/0018654 A1 | 1/2009 | Schmieding et al. |
| 2009/0030516 A1 | 1/2009 | Imbert |
| 2009/0054982 A1 | 2/2009 | Cimino |
| 2009/0062854 A1 | 3/2009 | Kaiser et al. |
| 2009/0082805 A1 | 3/2009 | Kaiser et al. |
| 2009/0187244 A1 | 7/2009 | Dross |
| 2009/0216326 A1 | 8/2009 | Hirpara et al. |
| 2009/0228017 A1 | 9/2009 | Collins |
| 2009/0234451 A1 | 9/2009 | Manderson |
| 2009/0265003 A1 | 10/2009 | Re et al. |
| 2009/0275950 A1 | 11/2009 | Sterrett et al. |
| 2009/0306776 A1 | 12/2009 | Murray |
| 2009/0306784 A1 | 12/2009 | Blum |
| 2009/0312776 A1 | 12/2009 | Kaiser et al. |
| 2010/0049258 A1 | 2/2010 | Dougherty |
| 2010/0049319 A1 | 2/2010 | Dougherty |
| 2010/0100182 A1 | 4/2010 | Barnes et al. |
| 2010/0145384 A1 | 6/2010 | Stone et al. |
| 2010/0145448 A1 | 6/2010 | Montes De Oca Balderas et al. |
| 2010/0211075 A1 | 8/2010 | Stone |
| 2010/0211173 A1 | 8/2010 | Bardos et al. |
| 2010/0249930 A1 | 9/2010 | Myers |
| 2010/0268273 A1 | 10/2010 | Albertorio et al. |
| 2010/0268275 A1 | 10/2010 | Stone et al. |
| 2010/0274355 A1 | 10/2010 | McGuire et al. |
| 2010/0274356 A1 | 10/2010 | Fening et al. |
| 2010/0292792 A1 | 11/2010 | Stone et al. |
| 2010/0305709 A1 | 12/2010 | Metzger et al. |
| 2010/0312341 A1 | 12/2010 | Kaiser et al. |
| 2010/0318188 A1 | 12/2010 | Linares |
| 2010/0324676 A1 | 12/2010 | Albertorio et al. |
| 2010/0331975 A1 | 12/2010 | Nissan et al. |
| 2011/0040380 A1 | 2/2011 | Schmieding et al. |
| 2011/0046734 A1 | 2/2011 | Tobis et al. |
| 2011/0054609 A1 | 3/2011 | Cook et al. |
| 2011/0087284 A1 | 4/2011 | Stone et al. |
| 2011/0098727 A1 | 4/2011 | Kaiser et al. |
| 2011/0112640 A1 | 5/2011 | Amis et al. |
| 2011/0112641 A1 | 5/2011 | Justin et al. |
| 2011/0118838 A1 | 5/2011 | Delli-Santi et al. |
| 2011/0137416 A1 | 6/2011 | Myers |
| 2011/0184227 A1 | 7/2011 | Altman et al. |
| 2011/0196432 A1 | 8/2011 | Griffis, III |
| 2011/0196490 A1 | 8/2011 | Gadikota et al. |
| 2011/0218625 A1 | 9/2011 | Berelsman et al. |
| 2011/0238179 A1 | 9/2011 | Laurencin et al. |

(56) References Cited

U.S. PATENT DOCUMENTS

| | | |
|---|---|---|
| 2011/0270278 A1 | 11/2011 | Overes et al. |
| 2011/0276137 A1 | 11/2011 | Seedhom et al. |
| 2011/0288635 A1 | 11/2011 | Miller et al. |
| 2011/0301707 A1 | 12/2011 | Buskirk et al. |
| 2011/0301708 A1 | 12/2011 | Stone et al. |
| 2012/0046746 A1 | 2/2012 | Konicek |
| 2012/0046747 A1 | 2/2012 | Justin et al. |
| 2012/0053630 A1 | 3/2012 | Denham et al. |
| 2012/0065732 A1 | 3/2012 | Roller et al. |
| 2012/0089143 A1 | 4/2012 | Martin et al. |
| 2012/0109299 A1 | 5/2012 | Li et al. |
| 2012/0123474 A1 | 5/2012 | Zajac et al. |
| 2012/0150297 A1 | 6/2012 | Denham et al. |
| 2012/0165938 A1 | 6/2012 | Denham et al. |
| 2012/0197271 A1 | 8/2012 | Astorino et al. |
| 2012/0296345 A1 | 11/2012 | Wack et al. |
| 2013/0023928 A1 | 1/2013 | Dreyfuss |
| 2013/0023929 A1 | 1/2013 | Sullivan et al. |

FOREIGN PATENT DOCUMENTS

| | | |
|---|---|---|
| DE | 201 01 791 U1 | 6/2001 |
| EP | 0 440 991 | 8/1991 |
| EP | 1 108 401 | 6/2001 |
| EP | 1 707 127 | 10/2006 |
| WO | WO 2007/002561 | 1/2007 |
| WO | WO 2008/091690 | 7/2008 |

* cited by examiner

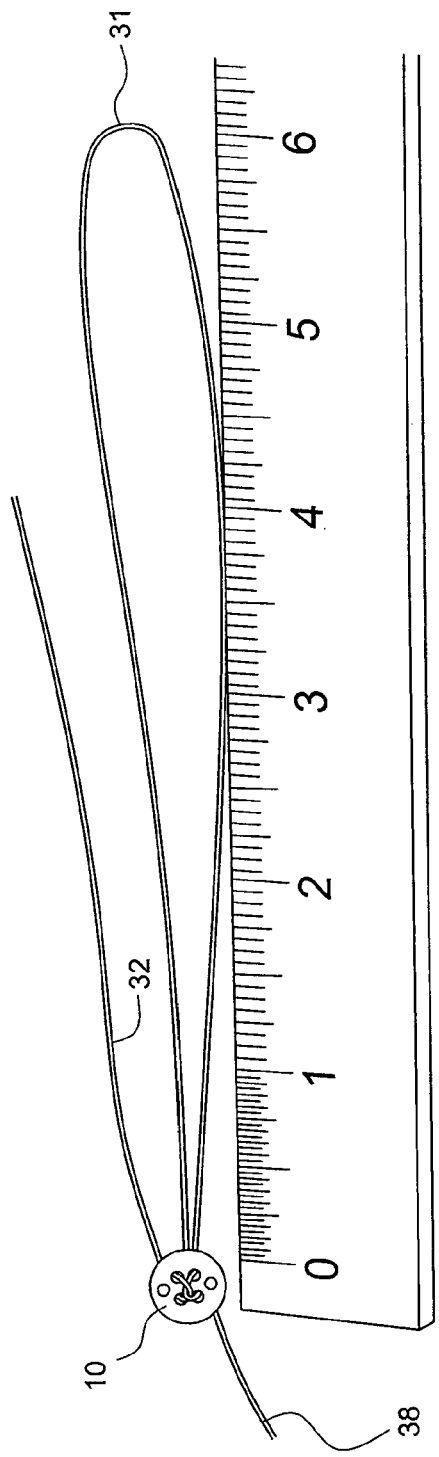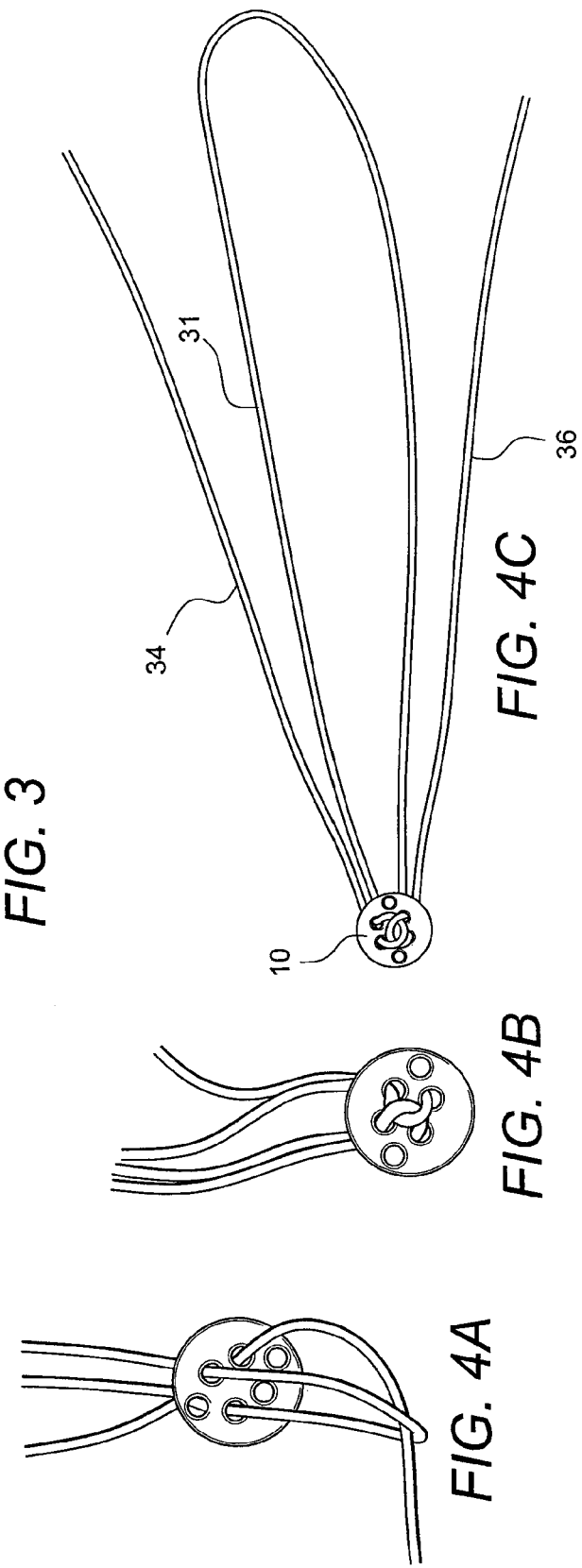

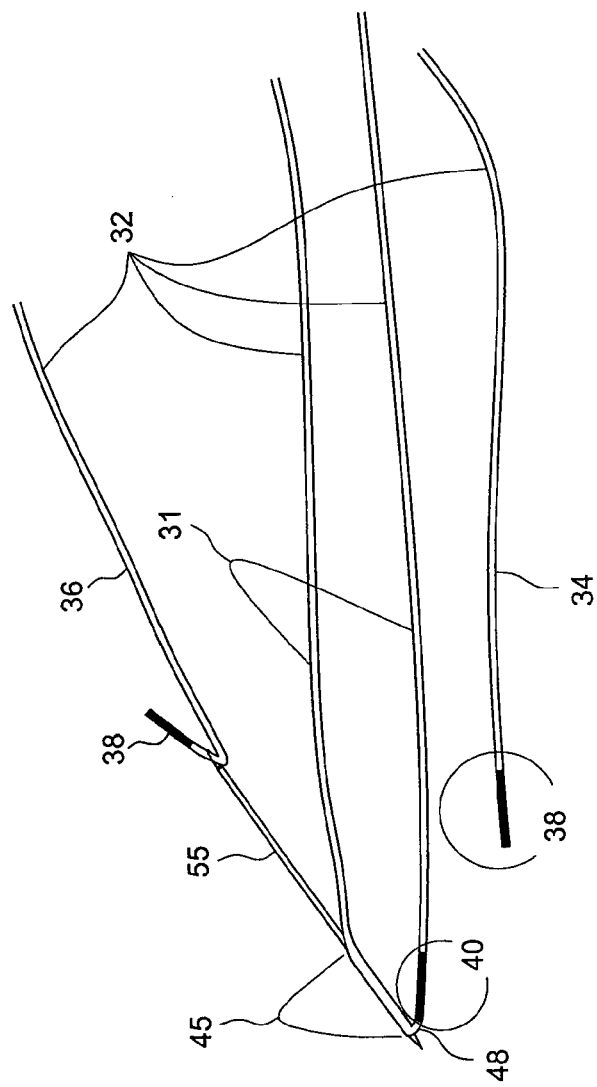
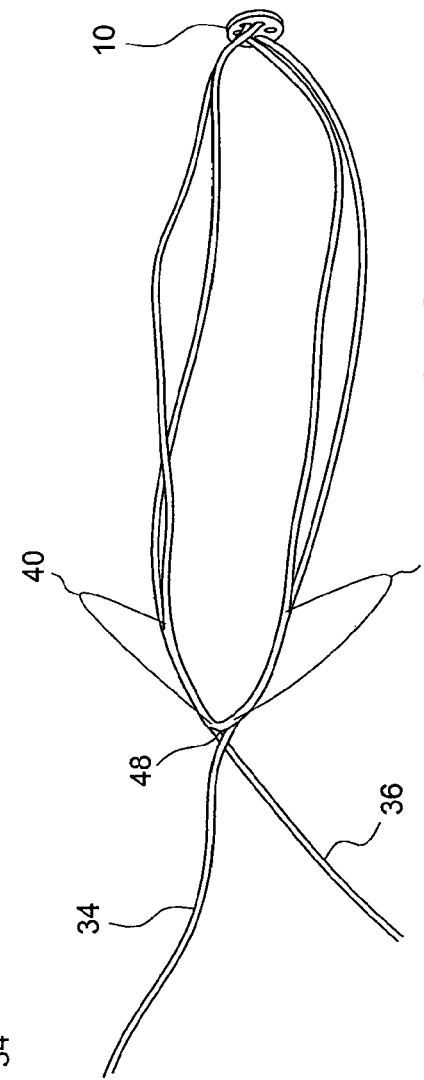

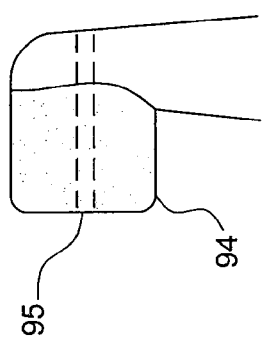
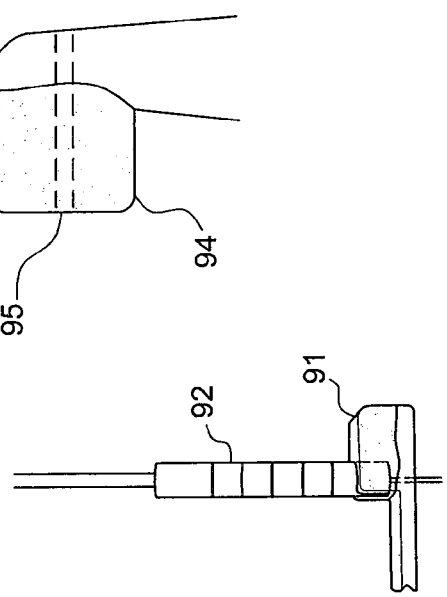
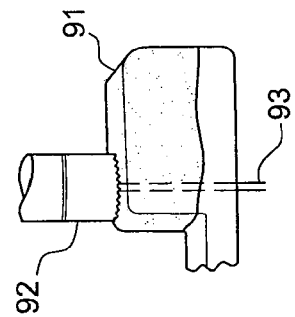
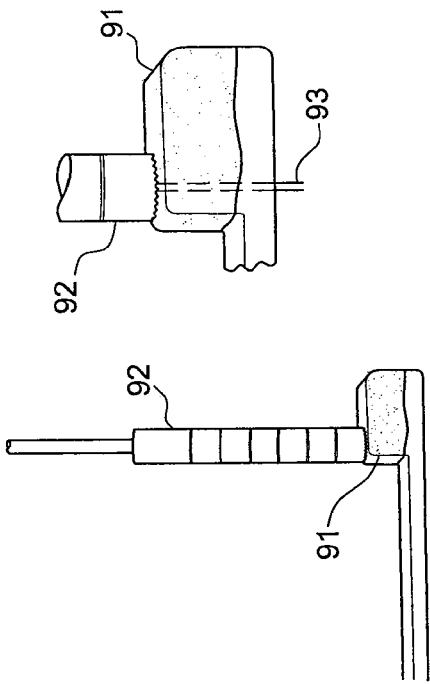
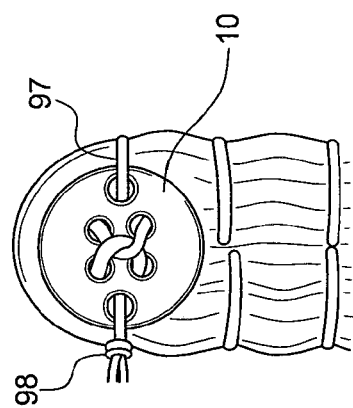
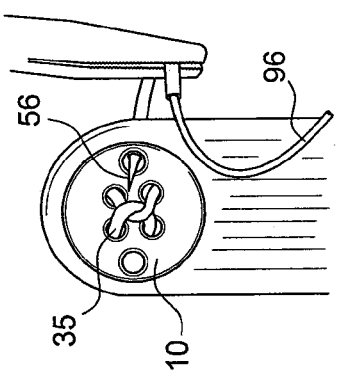
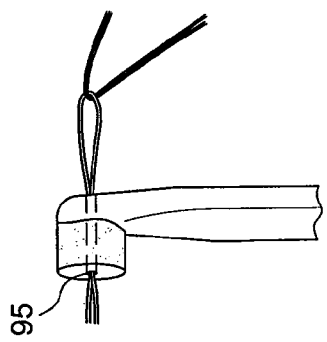

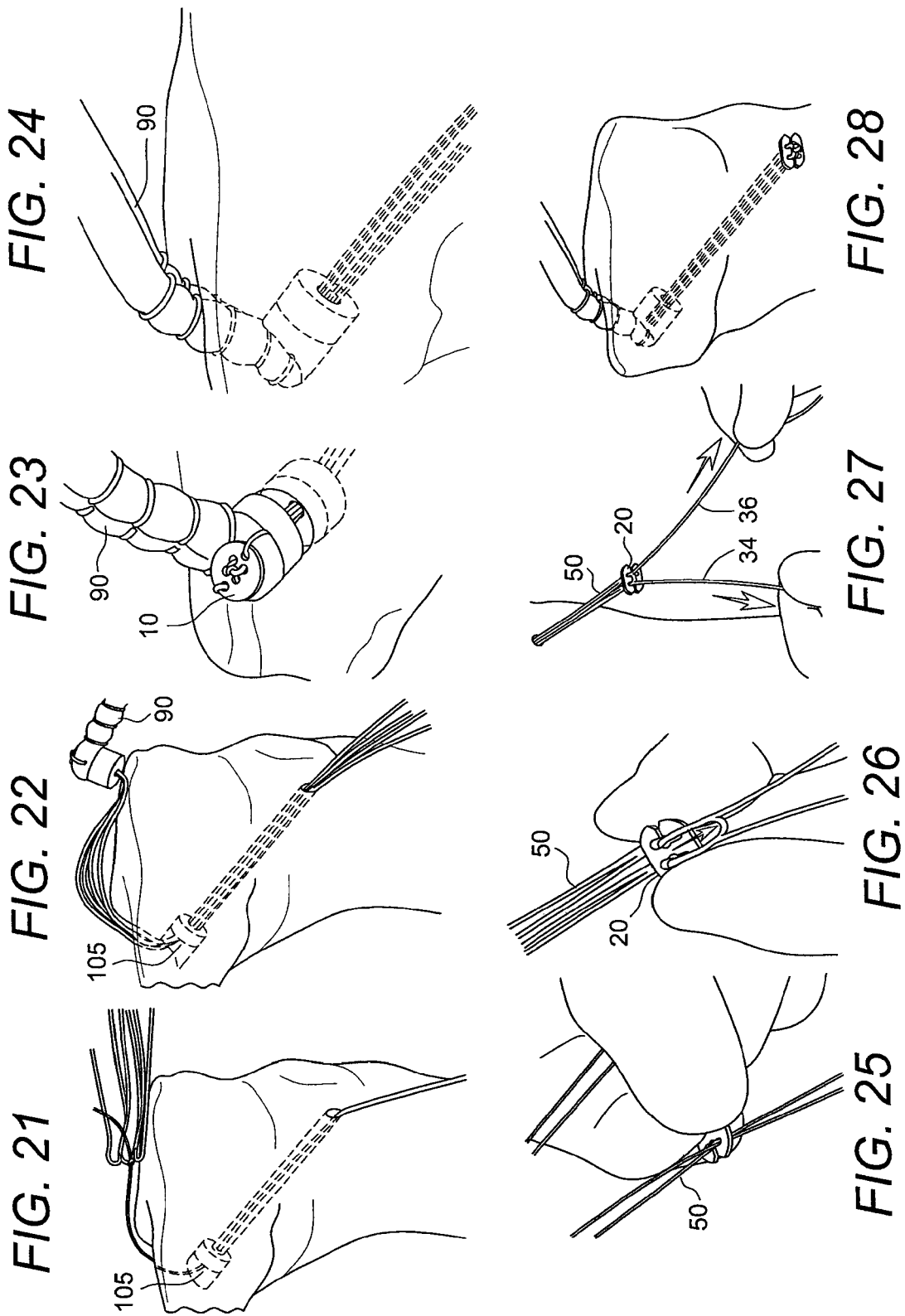

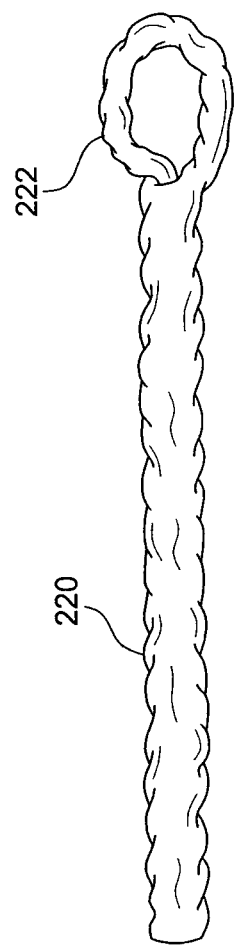
FIG. 47
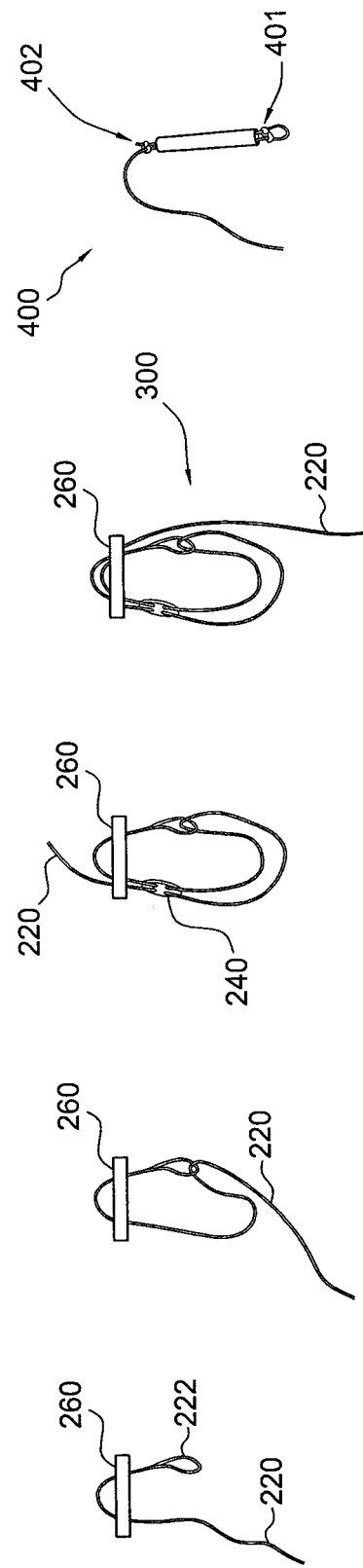
FIG. 48
FIG. 49
FIG. 50
FIG. 51
FIG. 52

ADJUSTABLE SUTURE-BUTTON CONSTRUCTS FOR LIGAMENT RECONSTRUCTION

CROSS-REFERENCE TO RELATED APPLICATIONS

This is a divisional of application Ser. No. 13/298,939, filed Nov. 17, 2011, now U.S. Pat. No. 8,591,578, which claims the benefit of U.S. Provisional Application No. 61/414,715, filed Nov. 17, 2010, the entire disclosures of which are incorporated by reference herein.

FIELD OF THE INVENTION

The present invention relates to the field of surgery and, more particularly, to ligament repair/reconstruction, such as, ACL and PCL repair/reconstruction techniques and associated fixation and reconstruction devices.

BACKGROUND OF THE INVENTION

The posterior cruciate ligament (PCL) is one of four ligaments important to the stability of the knee joint. The PCL prevents the tibia from sliding too far backwards. Along with the anterior cruciate ligament (ACL) which keeps the tibia from sliding too far forward, the PCL helps to maintain the tibia in position below the femur.

Surgical reconstruction of the PCL is usually recommended only for grade III PCL tears because of the overall technical difficulty of the surgery. Surgical PCL reconstruction is difficult in part because of the position of the PCL in the knee. Trying to place a new PCL graft in this position is challenging and, over time, the replacement PCL graft is notorious for stretching out and becoming less functional.

Adjustable suture-button constructs and associated techniques for fixation of a tendon or ligament, such as an ACL, are disclosed in U.S. Patent Application Publication No. 2010/0256677 and U.S. Patent Application Publication No. 2010/0268273, the disclosures of both of which are incorporated herein in their entirety. It would be desirable to provide similar adjustable suture-button constructs that can be used for PCL reconstruction, as well as for reconstruction of the ACL or collateral ligaments.

SUMMARY OF THE INVENTION

The present invention provides methods and constructs for ligament repair/reconstruction, such as PCL reconstruction and ACL reconstruction. The constructs use a knotless, adjustable, flexible suture loop, a first fixation device (a free or removable slotted button) and optionally a second fixation device (a fixed, non-removable button). Suture ends of the knotless suture loop provide a variable-length graft support that can be adjusted prior to, during, or after deployment of the constructs. The removable, detachable fixation device is provided with attachment feature(s) to permit assembly onto the adjustable loop. The removable, detachable fixation device is attached to one end of the loop, e.g., the tibia end of the loop construct after the loop construct is passed through the tibial tunnel (i.e., once the loop exits the anterior tibia cortex). If a fixed, non-removable button is employed, the fixed, non-removable button is securely attached (by stitching, for example) to the graft.

The present invention also provides a method of ligament repair by inter alia: (i) providing a ligament reconstruction system comprising an adjustable, self-locking, knotless, flexible, loop construct with a free or removable slotted button and optionally a fixed, non-removable button; and (ii) securing a PCL ligament, ACL ligament or other graft with the reconstruction system.

These and other features and advantages of the present invention will become apparent from the following description of the invention that is provided in connection with the accompanying drawings and illustrated embodiments of the invention.

BRIEF DESCRIPTION OF THE DRAWINGS

FIGS. 3-5 illustrate the steps for forming the knotless suture-button construct of FIG. 1.

FIG. 6 illustrates a perspective view of the reconstruction assembly resulting from the steps illustrated in FIGS. 3-5.

FIG. 10-16 illustrate an exemplary method of attaching a knotless suture-button construct with a fixed, graft button of the present invention to a graft to form a PCL graft construct.

FIGS. 18-28 illustrate a method of deploying the PCL reconstruction assembly of FIG. 17.

FIGS. 47-52 illustrate another adjustable, knotless suture construct of the present invention.

DETAILED DESCRIPTION OF THE INVENTION

Figure 1:
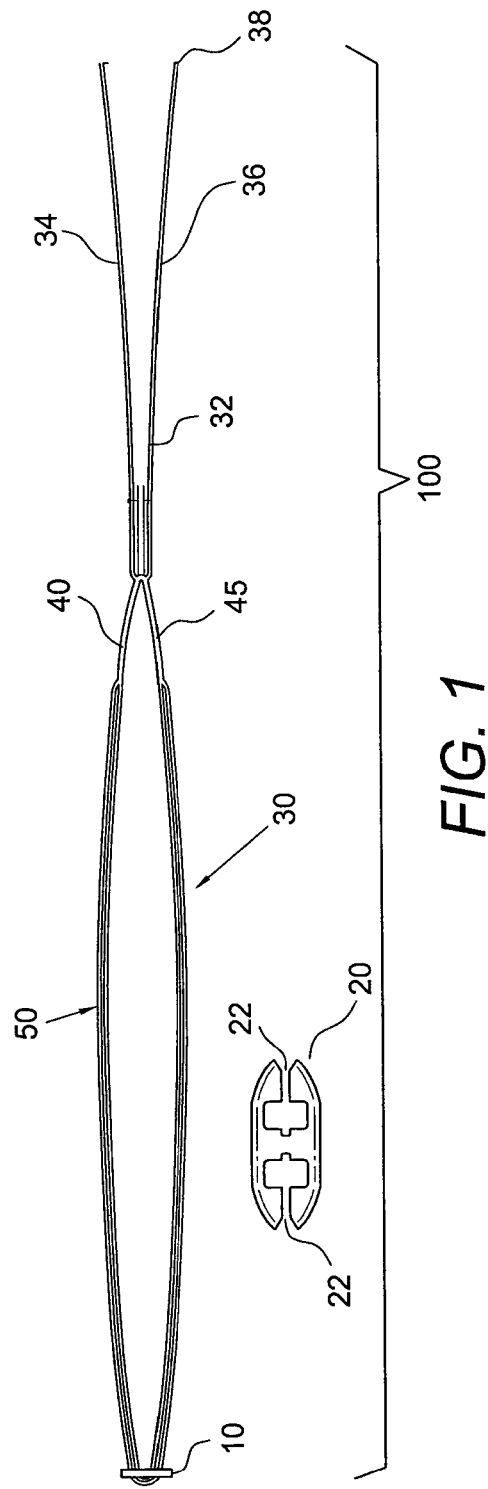
FIG. 1 illustrates a schematic view of a reconstruction assembly of the present invention, including a knotless suture-button construct with a fixed, graft button and a removable button (in the pre-assembled form) for ligament reconstruction, and according to a first embodiment of the present invention.

The present invention provides methods and reconstruction systems (knotless, adjustable loop constructs with a removable, detachable button) for ligament repair/reconstruction in a minimally invasive approach.

In embodiments of the present invention, methods and reconstruction systems (knotless, adjustable loop constructs with a removable, detachable button) for PCL/ACL repair/reconstruction in a minimally invasive approach In one embodiment, the reconstruction system comprises a suture-button construct formed by a first fixation device (for example, a graft button) attached to an adjustable, knotless flexible loop; and a free, removable, detachable second fixation device (for example, a slotted button). The graft button is preferably a round button (having four regular holes) with two small "extra" holes to allow stitching to the graft. The detachable button is slotted to allow assembly onto the loop construct. The detachable button is attached to the tibia end of the loop construct after the loop construct is passed through the tibial tunnel (i.e., once the loop exits the anterior tibia cortex). Tractable suture ends of the knotless suture loop provide a variable-length graft support that can be adjusted prior to, during, or after deployment of the constructs.

In another embodiment, the reconstruction system comprises an adjustable, knotless flexible loop and only one fixation device, i.e., only a free, removable, detachable button (without a fixed button). The removable, detachable fixation device is provided with attachment feature(s) to permit assembly onto the adjustable loop. Tractable suture ends of the knotless suture loop provide a variable-length graft support that can be adjusted prior to, during, or after deployment of the constructs.

In another embodiment, the reconstruction system comprises adjustable, knotless flexible loops and discrete fixation devices, one of which is a free, removable, detachable button (without a fixed button). The removable, detachable fixation device is provided with attachment feature(s) to permit assembly onto the adjustable loop. Tractable suture ends of the knotless suture loop provide a variable-length graft support that can be adjusted prior to, during, or after deployment of the constructs.

The present invention also provides methods of ligament repair by inter alia: (i) providing a ligament reconstruction system comprising an adjustable, self-locking, knotless loop construct with a detachable, free, removable button that is assembled onto the knotless loop construct (and optionally with a non-removable, graft button stitched to a graft); and (ii) securing a ligament or graft with the reconstruction system.

Referring now to the drawings, where like elements are designated by like reference numerals, FIGS. 1-28 illustrate reconstruction assembly 100 (with one fixed, suturable button and one removable, detachable button) and methods of PCL reconstructions (including arthroscopic inlay technique) with the assembly 100. The implant/assembly 100 (reconstruction system 100) of FIG. 1 includes an adjustable, knotless, flexible loop construct 50 formed from a flexible material 30 with button 10 to be attached to the graft (e.g., the graft button), by sewing or other suitable attachment techniques. A second, slotted button 20 which is capable of removable attachment to the tibial end of the loop construct after it is passed through the tibia (the detachable, removable button). Alternatively, the slotted button 20 is capable of removable attachment to adjustable, knotless, flexible loop construct 50 wherever deployed. Buttons 10 and 20 of the construct 100 may be formed, for example, of metal, PEEK or PLLA.

The graft button 10 is about 10 mm round button (having four regular holes) with two small "extra" holes to allow stitching to the graft. The detachable button 20 is about 12 mm×8 mm and is slotted to allow assembly onto the loop construct. The slots 22 will allow it to be loaded onto the thinner, proximal loop segment (non-spliced section) but will not allow passage of the thicker loop segment (spliced) near the tibia to prevent detachment from the implant. As detailed above, the buttons are provided with openings that allow the passage of the flexible material 30 to pass thereto. The detachable button 20 may be provided on a driver 60 that holds the button onto a "forked" tip to simplify loading. Once the detachable button 20 is loaded, the forked tip can be retracted by sliding a button on the handle, which will release the detachable button.

FIGS. 1 and 6 illustrate schematic and perspective views of assembly 100 of the present invention, in a pre-assembled form. Assembly 100 includes a knotless suture-button construct 50 formed of a knotless, flexible, adjustable suture member 30 formed from a flexible member 32 and a fixed, non-removable fixation device 10 (graft button 10) and a removable, detachable fixation device 20 (button 20). The flexible material 30 may be a high strength braid construct such as an ultrahigh molecular weight (UHMWPE) braid. The flexible material 30 may be provided with optional colored strands to assist surgeons in distinguishing between suture lengths with the trace and suture lengths without the trace. Assembly 100 may be provided as a kit of components. The knotless suture-button construct has an adjustable loop length and allows adjustment in one direction while preventing or locking the construct from loosening in the opposite direction, due to applied tensile forces.

Figure 2B:
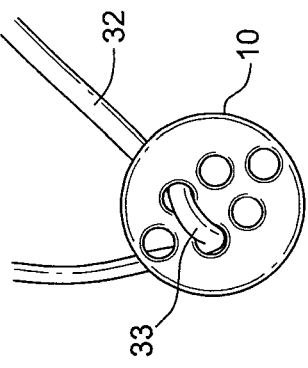
FIG. 2B is a top view of the intertwined threaded flexible member and fixed graft button.
Figure 2A:
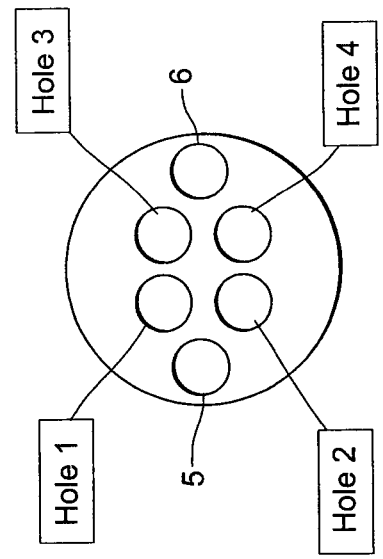
FIG. 2A illustrates the fixed, graft button of the knotless suture-button construct of FIG. 1.
Figure 8:
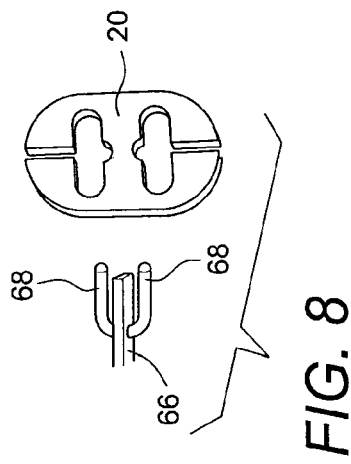
FIG. 8 is an enlarged view of the instrument head and the removable button.
Figure 7:
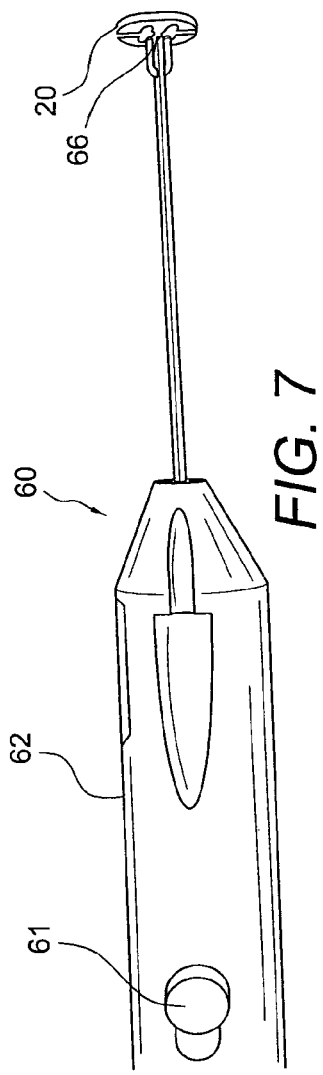
FIG. 7. illustrates a driver instrument for engaging the removable, detachable button.

FIG. 2A shows a top view of the first fixation device 10 used for the knotless suture-button construct 50 shown in FIG. 1. In an exemplary embodiment only, the first fixation device 10 is a round button provided with a plurality of circular holes. In an exemplary embodiment only, button 10 is a 10 mm diameter titanium button with 6 round holes, e.g., holes 1-4 and stitching holes 5 and 6. FIG. 2B illustrates the intertwined flexible member discussed in detail below with the flexible member cross-over "X" 35.

FIGS. 3, 4A-4C, 5 and 6 illustrate exemplary steps of forming the knotless suture-button construct 50 (with the following exemplary starting materials).

Starting Materials:
A braided high strength (UHMWPE) suture strand 32.
A needle with nitinol loop 55.
A round titanium button 10 with six holes.

Assembly Instructions for Reconstruction Assembly 100:
Step 1: One tail/end 38 of braid 30 is passed through hole 1, then back down through hole 2 of the button 10 (FIG. 2) forming a flexible member strand section 33 that bridges holes 1 and 2.

Step 2: About 12 inches of the longer strand (second tail) is passed through hole 3 adjacent to the first hole of button 10 to create a loop 31 (FIG. 3).

Step 3: The tail end 38 of the same strand that passed through hole 3 is passed under the strand section 33 bridging holes 1 and 2 and then passed over the strand section 33 and down through hole 4 of button 10 (FIGS. 2 and 4A-4C). This forms an intertwining or interlinking "X" 35 of the braid (FIGS. 2 and 4A-4C). The strand looped across holes 1 and 2 will be linked with the strand across holes 3 and 4.

Steps 4 and 5: The loop 30 is tightened to create an apex 48 at the center. One tail strand 34 is used to create an eyesplice 40 terminating at the apex 48 of the braid loop 30 (FIG. 5), where FIG. 5 is a partial view of the suture member 32 after it has been threaded through button 10. The first splice 40 is created by passing the blunt tip needle 55 and a tail end 38 through the center of the braid 30 with the strand being carried through in the nitinol loop of the needle 55. Step 5: Splicing is repeated with the remaining tail end (also 38) on the opposing side of the loop to form a second splice 45 of adjustable, knotless loop 30 (FIG. 5). FIG. 6 illustrates the adjustable, knotless construct with the button 10.

As button 10 is attached to flexible material 32 and includes two adjustable eyesplices 40, 45, pulling on the free braid strands 34, 36 respectively constricts the individual eyesplices 40, 45, and in turn, reduces the loop length of loop 30. In order for loop 30 to elongate, a force needs to be applied interior to one or both of the eyesplices to elongate the individual loops.

The slotted button 20 can be attached to the tibial end of the loop (to the proximal, thinner non-spliced loop segment) after it is passed through the tibia (the detachable, removable button 20). The graft button 10 may be an exemplary 10 mm round button (having four regular holes) with two small "extra" holes to allow stitching to the graft. The detachable button 20 may be an exemplary 12 mm×8 mm button and is slotted to allow assembly onto the loop construct.

Figure 9:
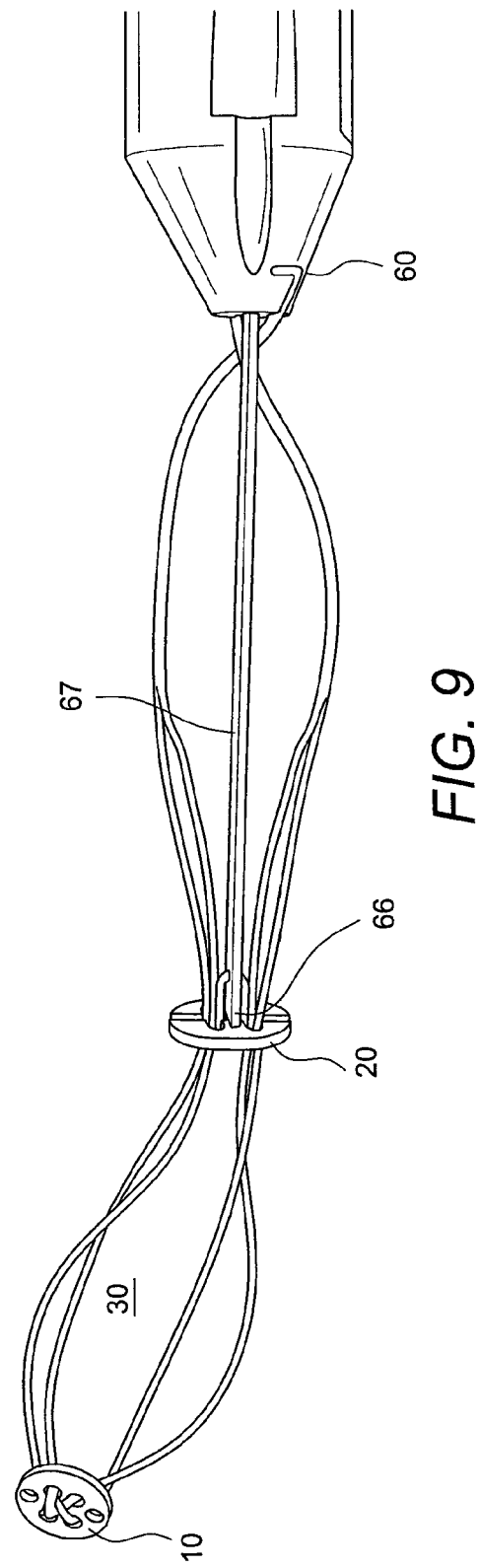
FIG. 9 illustrates loading of the removable, detachable button onto the knotless suture-button construct using the driver instrument.
Figure 17:
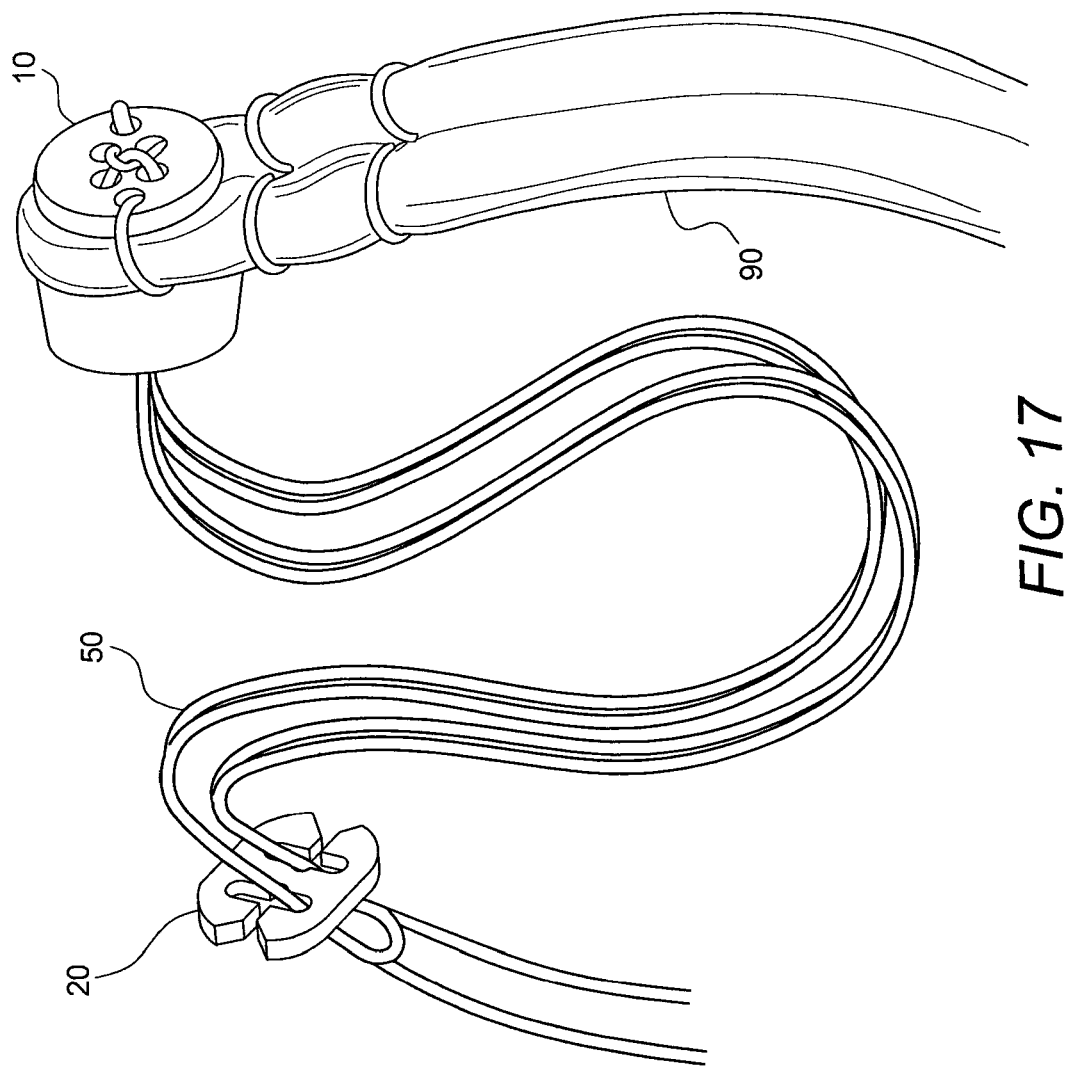
FIG. 17 illustrates a PCL graft construct of the present invention.

A driver instrument 60 (FIGS. 7-9) easily holds button 20 for loading. Driver 60 includes a "forked" tip 66 at the distal end of shaft 67 with prongs 68 which detachable hold button 20. Once the button 20 is loaded, the forked tip 66 can be retracted by sliding a button 61 on handle 62 of the driver 60, which will release the button 20. The button is released and pulled distally. The button cannot fall off the loop and the implant 100 can be tightened. FIG. 9 is a perspective view of the reconstruction assembly 100 of the invention, with fixed, graft button 10 and removable, detachable button 20 secured on knotless, adjustable, flexible suture loop (suture member) 50.

FIGS. 10-16 illustrate the exemplary steps followed to attach construct 100 to bone block 91 of the PCL graft 90. A method of assembling PCL graft construct involves inter alia the steps of: (i) providing at least one flexible, adjustable loop 50 construct (a four-point knotless fixation device) that is capable of adjusting tension (i.e., is provided with a loop having an adjustable perimeter and length); (ii) attaching the button 10 of the loop construct 50 to a bone block 91 of a PCL graft 90 by suturing the button 10 to the graft 90 through laterally arranged small holes that go through the bone block 91; (iii) passing the adjustable loop 50 through a tibial tunnel; (iv) assembling a detachable button 20 onto the loop of the construct 50 exiting the tibia (onto the thinner, non-spliced loop segment); and (v) subsequently, tightening the loop construct to fix the bone block portion of the PCL graft into the posterior socket.

FIGS. 10-13 illustrate one embodiment of preparing the graft 90. Place a coring reamer 92 next to the bone tendon junction in the desired location of the final graft. Use the reamer 92 to drill a 2.4 mm hole through the bone plug 91. Replace the drill pin with the collared pin 93 from the coring reamer. Ream until the blade reaches the tendon. Remove excess bone with a sagital saw and rongeur to form bone inlay 94 with passageway 95, until the graft fits in the appropriate sized hole in the sizing block.

Place a passing suture through button 10 and pass through hole 95 (FIG. 14). Pull the button 10 down tightly against the tendinous portion of the graft 90. Use the open holes in the button 10 to attach the button to the tendon 90. With needle 56 stitch the button 10 with suture 96 with whip stitches 97 and 98 (FIGS. 15-16). The attachable button 20 can be loaded onto the implant, over the anterior tibia and tensioned by pulling on shortening strands.

Figure 20:
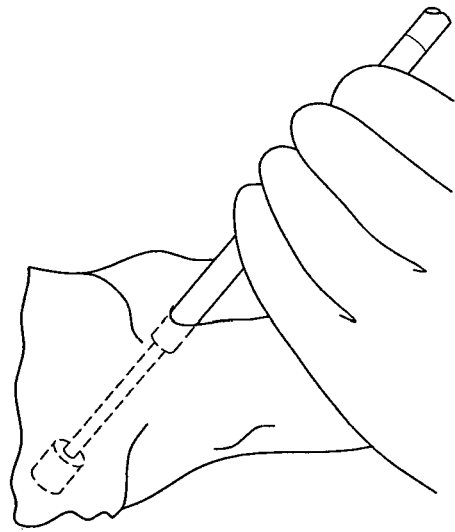
Figure 19:
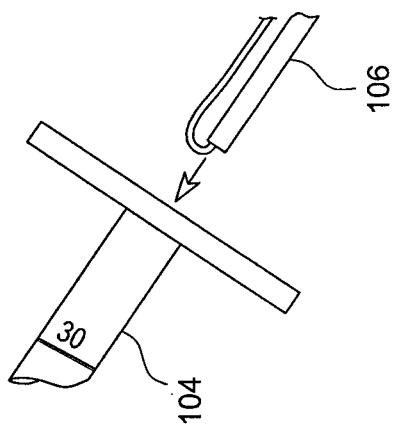
Figure 18:
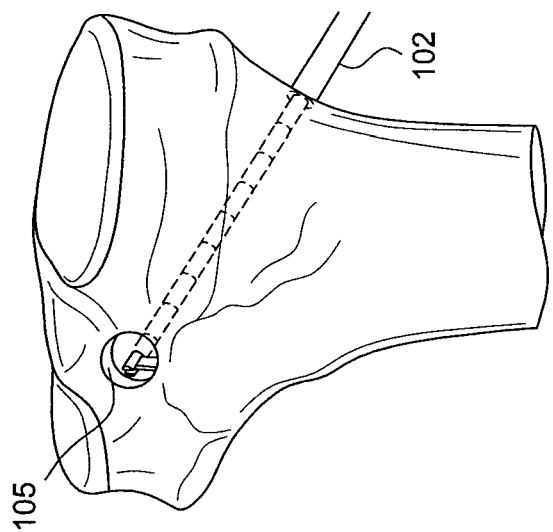

The adjustable suture-button construct of the present invention facilitates tibial fixation of the arthroscopic inlay technique. The arthroscopic inlay provides the benefits of traditional, open inlay PCL reconstruction with the advantage of being an arthroscopic procedure. As illustrated in FIGS. 18-20, use a guide and a drill for example, an Arthrex Retro-Construction™ Guide and a FlipCutter®) about equal to the size of the reamer 92 to drill a socket 105 approximately 12 mm deep over the PCL tibial insertion site. Remove the FlipCutter® 102 from the drill sleeve 104 while holding sleeve in place for suture passing. Pass passing suture 106 (for example, a #2 Fiberstick™) through the drill sleeve and into the joint for retrieval through the anteromedial portal.

As illustrated in FIGS. 21-24, a wire (passing suture) is retrieved from the joint through a peripatellar arthroscopy portal, and then utilized to introduce the graft/implant 100 into the knee. An arthroscopic grasper to hold the graft 90 at the tendon bone junction inferiorly and push the graft posterior until it reaches the tibial socket. Hold light tension on the implant (not tensioning strands) to guide the graft 90 into position. When the bone block 94 of the graft 90 has reached the tibial socket, as seen arthroscopically and fluoroscopically, pull distally to seat graft 90. Once the loop construct exits the anterior tibial cortex, button 20 with attachment features (such as slots, for example) is assembled by the surgeon onto the loop and sliding the button 20 distally to the end of the implant. (FIGS. 25 and 26). Tension strands 34, 36 of the implant/construct symmetrically and remove any slack buildup created by one strand by pulling on the other, then pull to cinch up the loop construct and fix the bone block portion of the graft into the posterior socket. (FIGS. 27-28). The suture is thicker in the end of the implant, ensuring that the button 20 cannot become disassembled from the suture. Once the graft 90 is seated, the tensioning strands may be cut. A knot may be tied before cutting sutures, to protect the implant during cutting and to act as backup fixation. Proceed with femoral graft passing and fixation.

FIGS. 29-46 illustrate other exemplary fixation assemblies of the present invention and associated methods of ligament reconstructions, e.g., for ACL repair. In one embodiment two reconstruction assemblies 100 are provided with only removable, detachable buttons 20. In another embodiment, reconstruction assembly 100 with a removable button and a second reconstruction assembly 200 with a fixed oblong button are used with graft 190.

Figure 29:
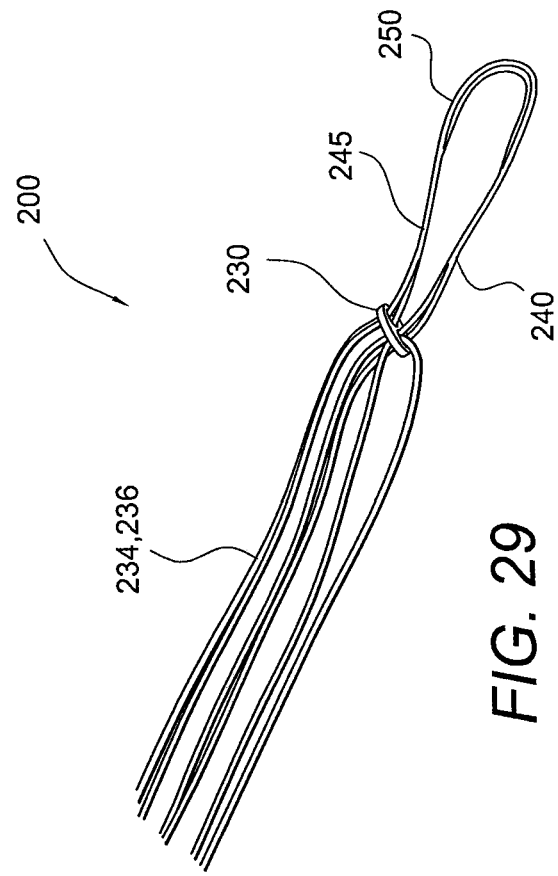
FIG. 29 illustrates another suture-button construct for use with the present invention.
Figure 33:
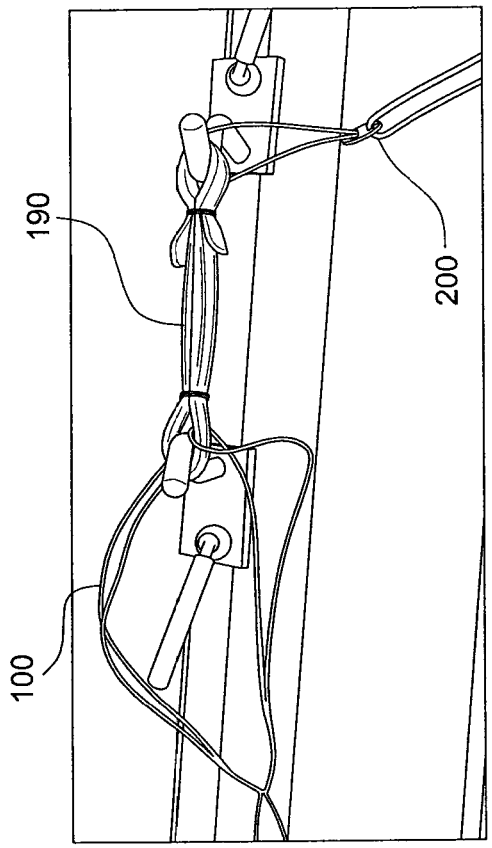

FIG. 29 illustrates the reconstruction assembly 200 with fixed button 230 and the adjustable, knotless, flexible suture construct 250, similar to construct 50, with splices 240, 245. As with reconstruction assembly 100, reconstruction assembly 200 includes the adjustable knotless suture construct of the present invention formed from an open ended, flexible member, for example, a braided suture, and is formed in a similar manner. A first suture tail shortening strand (a free suture end) of the flexible member is spliced through a first segment of the suture on one side of a mid-section of the flexible member. A first adjustable loop "1" is formed. A second suture tail, shortening strand (the other free suture end) is first passed through the loop 1 and then spliced through a second segment of the suture on another side of the mid-section to form the adjustable suture construct, illustrated above. The first and second segments are off-set and separate from one another. Pulling on the free ends of the suture (i.e., the shortening strands) adjusts the length of the graft support.

Figure 30:
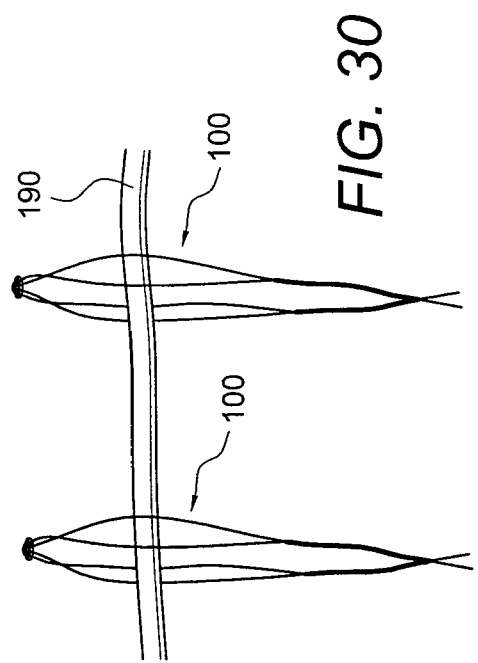
FIGS. 30-33 illustrate the assembly of additional ligament-construct embodiments using adjustable knotless loop constructs of the present invention.
Figure 31:
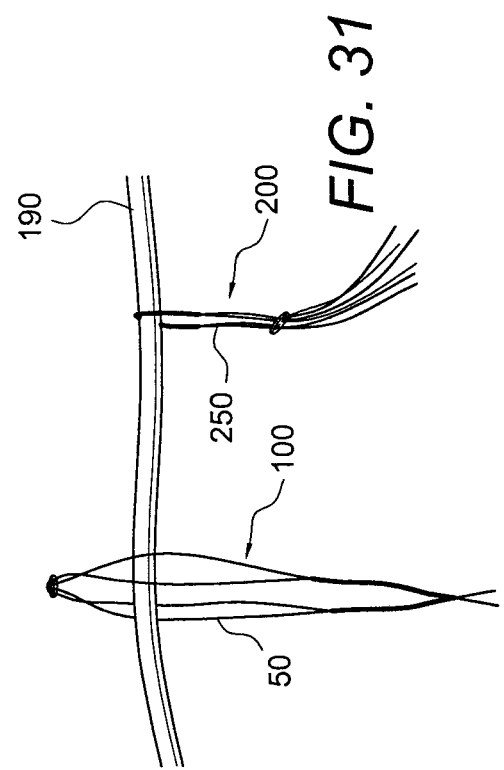

Suture-button constructs 50, each without a button, are loaded onto the graft 190. (FIG. 30). Alternatively, suture-button construct 50 with a detachable button and any suitable adjustable suture-button construct, such as the ACL suture-button construct 200 with a fixed button are loaded on respective sides of graft 190, as illustrated in FIG. 31. Once loaded, the graft 190 is folded into a loop and sutured to create a graft construct 190 ("GraftLink®"), FIGS. 32 and 33.

Figure 35:
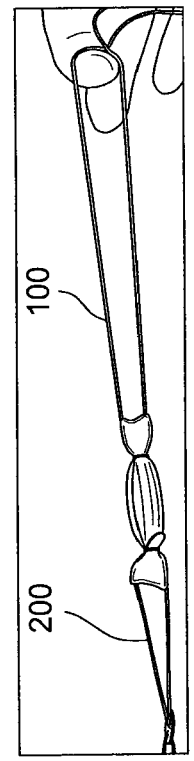
FIGS. 34-46 illustrate the exemplary steps practiced in deploying the ligament-constructs of FIGS. 30-33.
Figure 32:
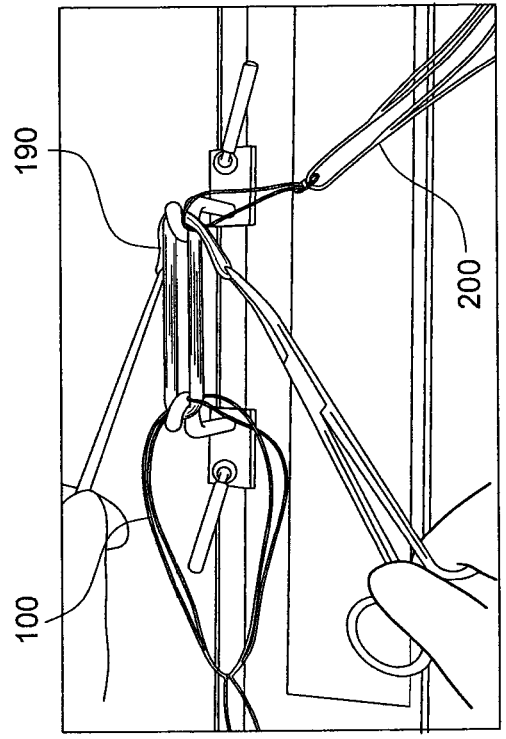
Figure 34:
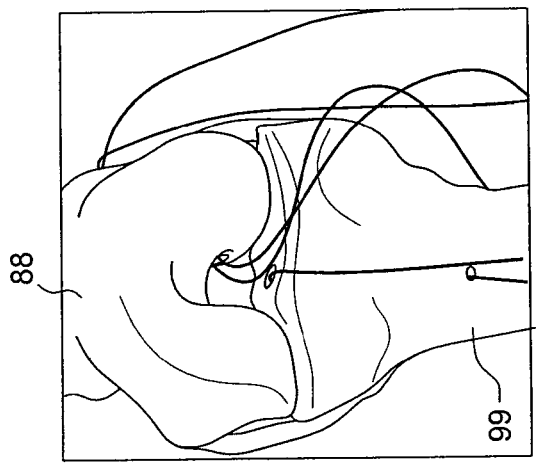
Figure 41:
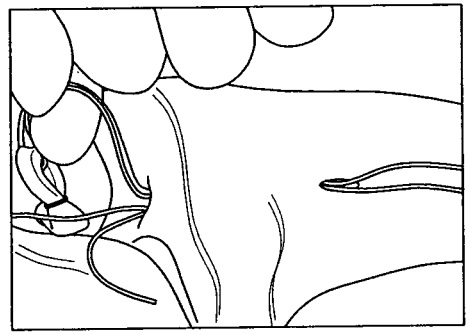
Figure 40:
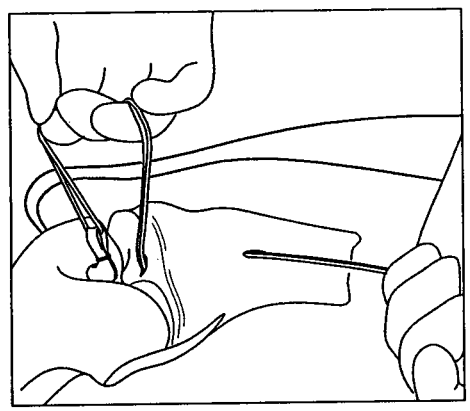
Figure 37:
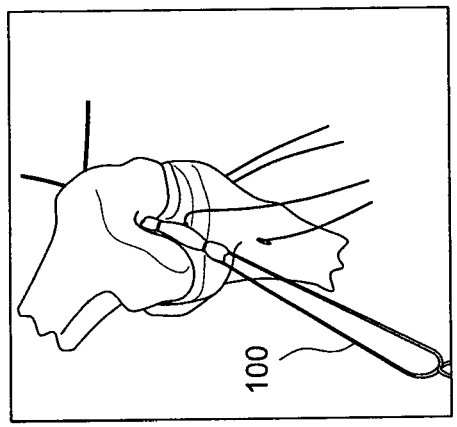
Figure 39:
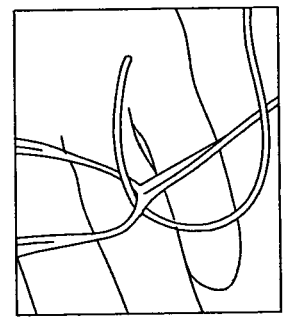
Figure 36:
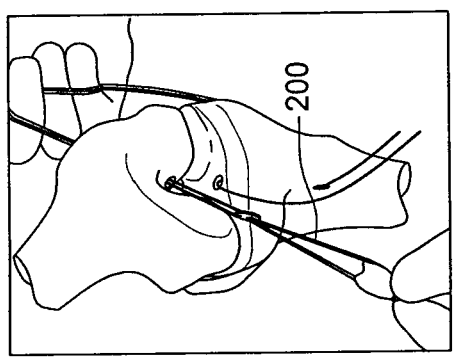
Figure 38:
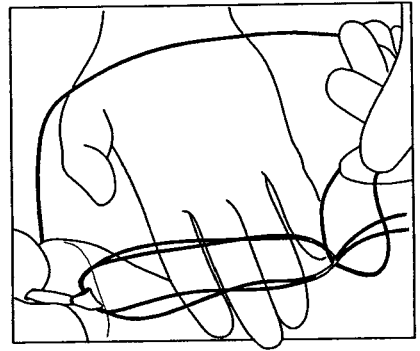

Femoral and tibial sockets are prepared in the knee, the passing sutures placed, and graft 190 is taken off preparation station, FIGS. 34 and 35. The femoral adjustable suture-button construct 200 (or 100) is passed and the shortening strands are pulled to advance graft to femur (FIGS. 36-37). In the case of two adjustable suture-button constructs 100, one is similarly passed and pulled through the femoral tunnel.

Figure 44:
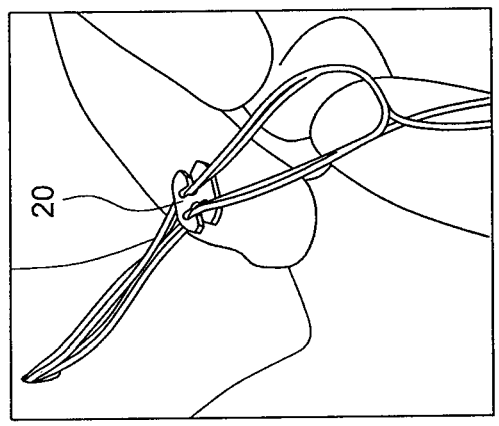
Figure 43:
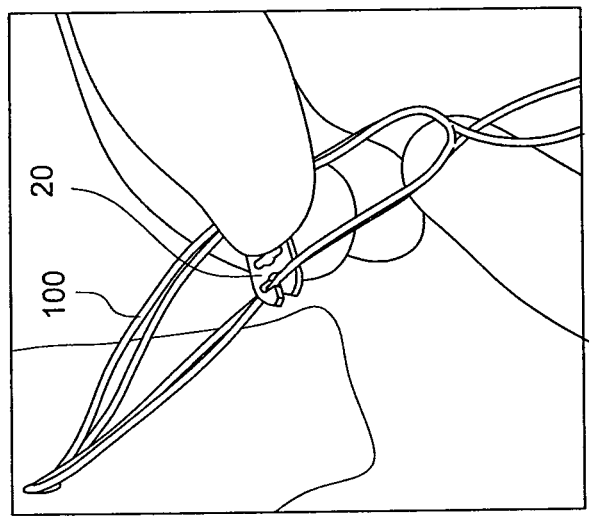
Figure 42:
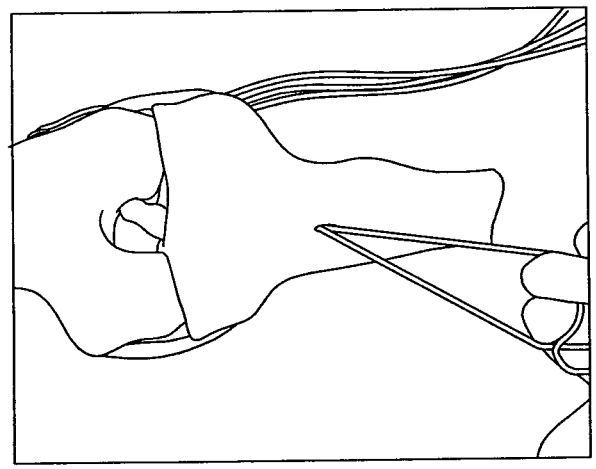

As illustrated in FIGS. 38-42, the tibial passing suture is tied to adjustable suture-button construct 100 which includes a removable button to be subsequently assembled and passed through the tibia. The tibial construct 100 is passed through the tibia completely, and button 20 loaded by sliding the proximal, thinner part of loop 50 through the slots 22 of button 20 (FIGS. 43 and 44).

Figure 46:
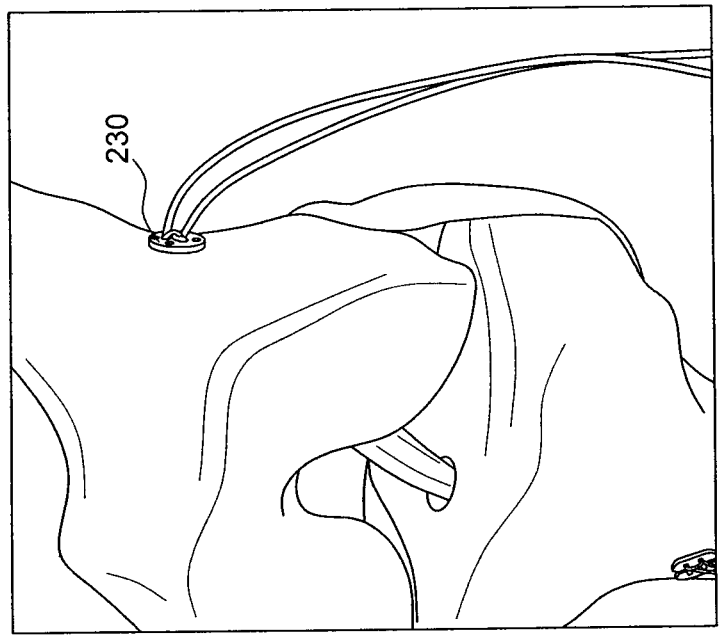
Figure 45:
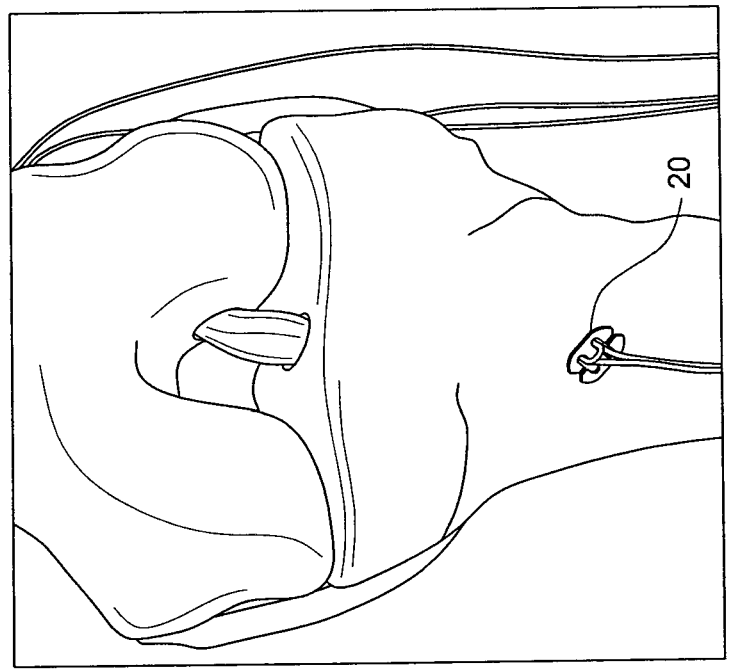

FIGS. 45-46): The button 20 is pulled down to the end of the loop 50, near the tensioning sutures 34 and 36. The tensioning sutures are then pulled to shorten the implant which brings the button to bone and tensions the graft. After appropriate graft tension is reached sutures may be cut and surgery is complete. A knot (for example, a square knot) may be tied over the button 20 to protect the splice from being damaged and as backup fixation to the self locking suture-button construct.

FIGS. 47-52 illustrate another suture-button construct 300 of the present invention including one adjustable and one fixed loop. The suture-button construct 300 may be used in conjunction with a detachable, removable button (such as button 20 described above) for the PCL repair detailed above, or for any other fixation of tissue in surgical repairs.

FIG. 47 shows a strand of flexible material 220 (for example, an UHMWPE braid 220) with a fixed eyesplice 222 at one end (fixed by stitching/interweaving individual strands, as known in the art) to be passed through button 260. FIGS. 48-52 illustrate sequential exemplary steps of a method of forming/assembling construct 300 (FIG. 51) of the present invention. The construct includes one adjustable and one fixed loop, with an adjustable splice 240 (FIG. 50). One strand controls the length of the loop, eliminating the need to construct multiple loops evenly. Stitching is one option for the fixed eyesplice but may include other methods of locking/creating the fixed splice. For example, one such alternative is tying knots 401, 402 at either end of an adjustable splice (as shown in FIG. 52) to form construct 400. The knots 401, 402 are too bulky to pass through the splice tunnel and prevent adjustment of the splice loop. This results in a strong fixed loop without stitching.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is not to be considered as limited by the foregoing description.

What is claimed as new and desired to be protected by Letters Patent of the United States is:

1. A fixation system for ligament repair, comprising:
   an adjustable suture-button construct having a flexible, adjustable, knotless, continuous loop with two adjustable eyesplices that are interconnected for knotless fixation; a first fixation device comprising an oblong button having laterally arranged end slots to attachment to and detachment from the flexible, adjustable, knotless, continuous loop; a second fixation device comprising a round button with six holes secured to the flexible, adjustable, knotless, continuous loop; and a PCL graft secured to the round button by a suture.

2. The fixation system of claim 1, wherein the adjustable loop is formed of a high strength suture.

\* \* \* \* \*